United States Patent
Jin et al.

(10) Patent No.: US 11,607,191 B2
(45) Date of Patent: Mar. 21, 2023

(54) ULTRASOUND DIAGNOSIS APPARATUS AND METHOD OF ACQUIRING SHEAR WAVE ELASTICITY DATA WITH RESPECT TO OBJECT CROSS-SECTION IN 3D

(71) Applicant: SAMSUNG MEDISON CO., LTD., Hongcheon-gun (KR)

(72) Inventors: Gil-ju Jin, Hongcheon-gun (KR); Deok-gon Kim, Hongcheon-gun (KR); Sun-mo Yang, Hongcheon-gun (KR); Hyoung-ki Lee, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 586 days.

(21) Appl. No.: 15/594,843

(22) Filed: May 15, 2017

(65) Prior Publication Data

US 2018/0168542 A1 Jun. 21, 2018

(30) Foreign Application Priority Data

Dec. 21, 2016 (KR) .................. 10-2016-0175841

(51) Int. Cl.
*A61B 8/00* (2006.01)
*A61B 8/08* (2006.01)
(Continued)

(52) U.S. Cl.
CPC .............. *A61B 8/14* (2013.01); *A61B 8/4483* (2013.01); *A61B 8/4488* (2013.01); *A61B 8/465* (2013.01);
(Continued)

(58) Field of Classification Search
CPC ......... A61B 8/14; A61B 8/485; A61B 8/4488; A61B 8/4494; A61B 8/469;
(Continued)

(56) References Cited

U.S. PATENT DOCUMENTS 7,798,965 B2  9/2010  Torp et al.
8,187,187 B2  5/2012  Fan et al.
(Continued)

FOREIGN PATENT DOCUMENTS

JP  4964865 B2  7/2012
KR  100742463 B1  7/2007
(Continued)

OTHER PUBLICATIONS

Min Guo et al., "Quasi-plane shear wave propagation induced by acoustic radiation force with a focal line region: a simulation study", Australasian Physical and Engineering Sciences in Medicine, vol. 39, No. 1, Jan. 14, 2016, pp. 187-197, XP035966579. (11 pages total).

(Continued)

*Primary Examiner* — Serkan Akar
*Assistant Examiner* — Amal Aly Farag
(74) *Attorney, Agent, or Firm* — Sughrue Mion, PLLC

(57) ABSTRACT

An ultrasound diagnosis apparatus includes a two-dimensional (2D) array ultrasound probe configured to emit focused beams onto focusing points and detect echo signals; and a processor configured to determine the focusing points on a cross-section of interest and acquire shear wave elasticity data with respect to the cross-section of interest based on the detected echo signals.

15 Claims, 14 Drawing Sheets

(51) Int. Cl.
*A61B 8/14* (2006.01)
*G01S 7/52* (2006.01)
*G01S 15/89* (2006.01)
*G10K 11/34* (2006.01)

(52) U.S. Cl.
CPC .............. *A61B 8/483* (2013.01); *A61B 8/485* (2013.01); *G01S 7/52022* (2013.01); *G01S 7/52042* (2013.01); *G01S 7/52073* (2013.01); *G01S 15/8925* (2013.01); *A61B 8/4405* (2013.01); *A61B 8/4427* (2013.01); *A61B 8/4472* (2013.01); *A61B 8/4494* (2013.01); *A61B 8/464* (2013.01); *A61B 8/467* (2013.01); *A61B 8/469* (2013.01); *G01S 15/8993* (2013.01); *G10K 11/34* (2013.01)

(58) Field of Classification Search
CPC ............. G01S 7/52022; G01S 7/52073; G01S 15/8925; G10K 11/34
See application file for complete search history.

(56) References Cited

U.S. PATENT DOCUMENTS

| | | | |
|---|---|---|---|
| 2005/0165306 A1* | 7/2005 | Zheng | A61B 8/485 600/437 |
| 2009/0124901 A1 | 5/2009 | Fink et al. | |
| 2011/0144499 A1* | 6/2011 | Yoo | A61B 8/14 600/443 |
| 2013/0058195 A1 | 3/2013 | Cloutier et al. | |
| 2013/0296698 A1 | 11/2013 | Fraser et al. | |
| 2014/0046183 A1 | 2/2014 | Park et al. | |
| 2014/0058266 A1* | 2/2014 | Call | A61B 8/585 600/443 |
| 2014/0081135 A1 | 3/2014 | Choi et al. | |
| 2014/0148698 A1 | 5/2014 | Tamano | |
| 2014/0371593 A1* | 12/2014 | Kondoh | A61B 8/5223 600/443 |
| 2015/0018684 A1* | 1/2015 | Abe | A61B 8/14 600/443 |
| 2015/0148674 A1 | 5/2015 | Park et al. | |
| 2015/0150535 A1 | 6/2015 | Fan et al. | |
| 2015/0164476 A1* | 6/2015 | Kong | A61B 8/5207 600/438 |
| 2015/0192547 A1* | 7/2015 | Lee | G01N 29/04 73/641 |
| 2015/0209013 A1* | 7/2015 | Tsymbalenko | A61B 8/483 600/440 |
| 2016/0256135 A1* | 9/2016 | Susumu | A61B 8/485 |

FOREIGN PATENT DOCUMENTS

| | | |
|---|---|---|
| KR | 1020140020486 A | 2/2014 |
| KR | 1020140036650 A | 3/2014 |
| WO | 2016/102991 A1 | 6/2016 |

OTHER PUBLICATIONS

Min Guo et al., "A Rod-Like Acoustic Radiation Force in Ultrasound-Based Elastography: A Simulation Study", IFMBE Proceedings, vol. 42, Jan. 1, 2014, pp. 148-149, Springer International Publishing, Switzerland, XP055433671. (2 pages total).

Communication dated Dec. 21, 2017 by the European Patent Office in counterpart European Patent Application No. 17167978.0.

* cited by examiner

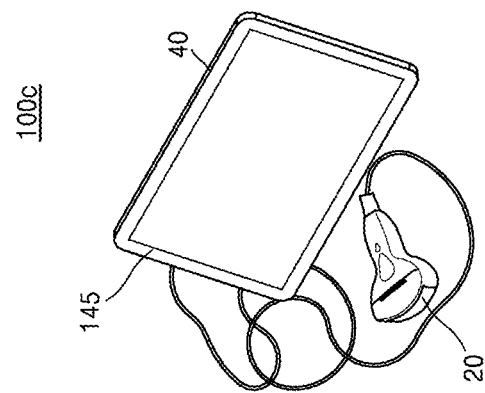
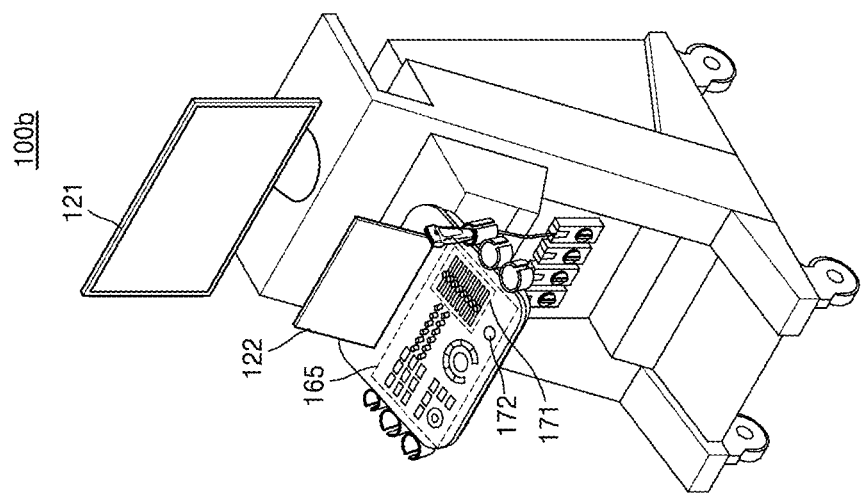
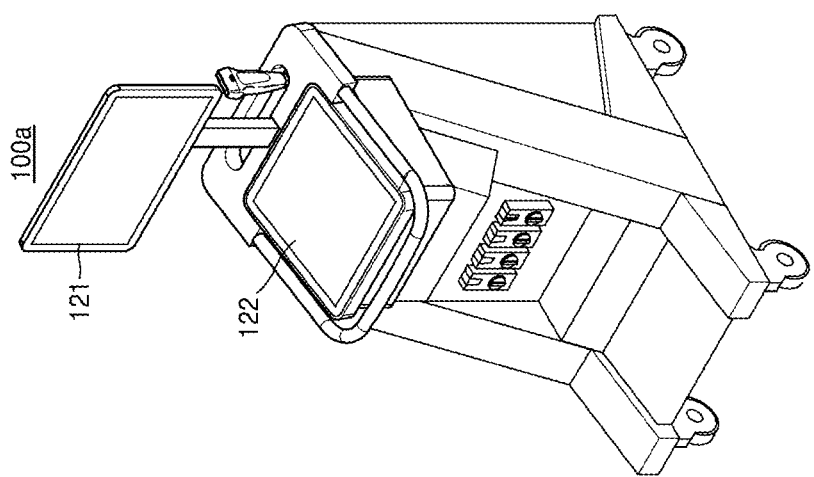

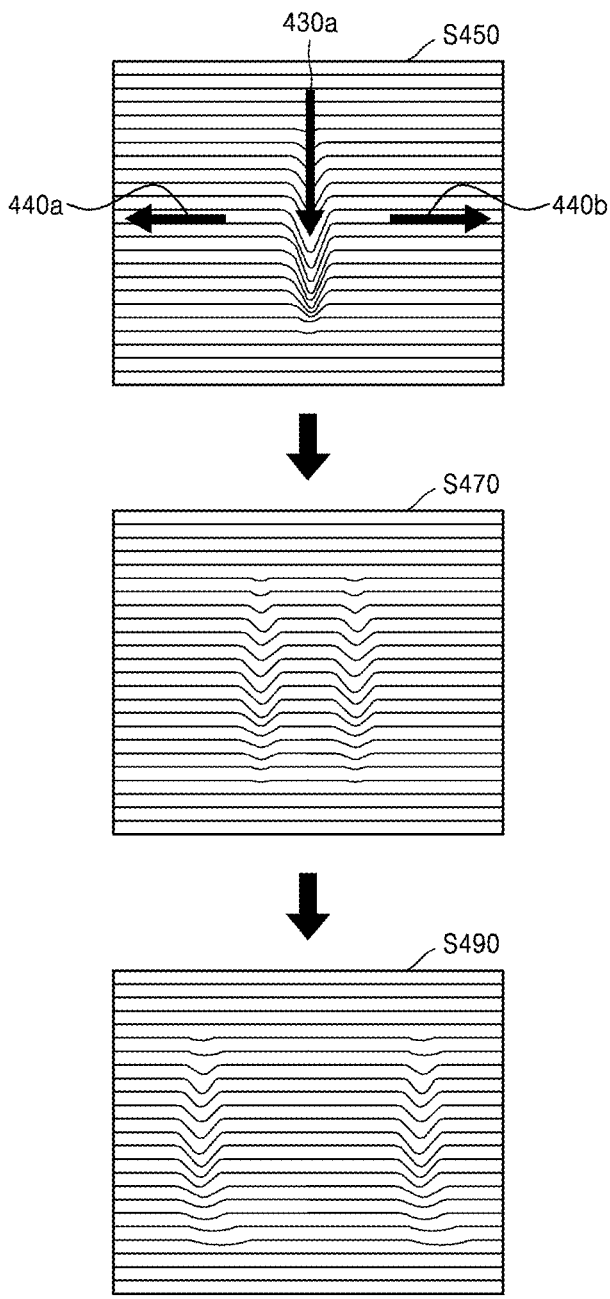

ULTRASOUND DIAGNOSIS APPARATUS AND METHOD OF ACQUIRING SHEAR WAVE ELASTICITY DATA WITH RESPECT TO OBJECT CROSS-SECTION IN 3D

CROSS-REFERENCE TO RELATED APPLICATION

This application claims the benefit of Korean Patent Application No. 10-2016-0175841, filed on Dec. 21, 2016, in the Korean Intellectual Property Office, the disclosure of which is incorporated herein in its entirety by reference.

BACKGROUND

1. Field

The present disclosure relates to ultrasound diagnosis apparatuses, methods of controlling the ultrasound diagnosis apparatuses, and computer-readable recording media having recorded thereon program code for performing the methods of controlling the ultrasound diagnosis apparatuses.

2. Description of the Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

Such ultrasound diagnosis apparatuses provide high stability, display images in real time, and are safe due to there being no radiation exposure, compared to X-ray diagnosis apparatuses. Therefore, an ultrasound diagnosis apparatus is widely used together with other types of imaging diagnosis devices.

SUMMARY

Provided are methods and ultrasound diagnosis apparatuses of acquiring shear wave elasticity data with respect to a cross-section of an object in a three-dimensional (3D) space based on a plurality of focusing points.

Provided are methods and ultrasound diagnosis apparatuses of converging energy to a region of interest (ROI) of an object, including a lesion, in a 3D space.

Additional aspects will be set forth in part in the description which follows and, in part, will be apparent from the description, or may be learned by practice of the presented embodiments.

According to an aspect of an embodiment, an ultrasound diagnosis apparatus includes: a two-dimensional (2D) array ultrasound probe configured to emit focused beams onto a plurality of focusing points and detect echo signals; and a processor configured to determine the plurality of focusing points on a cross-section of interest and acquire shear wave elasticity data with respect to the cross-section of interest based on the detected echo signals.

The 2D array ultrasound probe may be further configured to simultaneously emit the focused beams onto the plurality of focusing points.

The plurality of focusing points may be points lying on a straight line in the cross-section of interest.

The processor may be further configured to determine element groups respectively corresponding to positions of the plurality of focusing points among a 2D matrix array in the 2D array ultrasound probe.

The processor may be further configured to determine a plurality of points lying on a first straight line in the cross-section of interest as a first focusing group and determine a plurality of points on a second straight line in the cross-section of interest, which is distinguished from the first straight line, as a second focusing group, and the plurality of focusing points may include the plurality of points in the first focusing group, lying on the first straight line, and the plurality of points in the second focusing group, lying on the second straight line.

The 2D array ultrasound probe may be further configured to simultaneously emit the focused beams onto the plurality of points in the first focusing group and the plurality of points in the second focusing group.

The 2D array ultrasound probe may be further configured to emit focused beams onto the plurality of points in the first focusing group and to emit, after a lapse of a first time interval, focused beams onto the plurality of points in the second focusing group.

The ultrasound diagnosis apparatus may further include a user input interface configured to receive an input of at least one of the cross-section of interest of an object in a 3D space, the number of the plurality of focusing points, and an interval between each of the plurality of focusing points.

The ultrasound diagnosis apparatus may further include a display configured to display the acquired shear wave elasticity data.

According to an aspect of another embodiment, a method of controlling an ultrasound diagnosis apparatus includes: determining a plurality of focusing points on a cross-section of interest; emitting focused beams onto the determined plurality of focusing points and detecting echo signals; and acquiring shear wave elasticity data with respect to the cross-section of interest based on the detected echo signals.

According to an aspect of another embodiment, a computer-readable recording medium has recorded thereon computer program code for performing the method of controlling an ultrasound diagnosis apparatus.

BRIEF DESCRIPTION OF THE DRAWINGS

These and/or other aspects will become apparent and more readily appreciated from the following description of the embodiments, taken in conjunction with the accompanying drawings in which:

FIGS. 2A, 2B, and 2C are diagrams respectively illustrating an ultrasound diagnosis apparatus according to an exemplary embodiment;

FIG. 4B illustrates propagation of shear waves according to an embodiment;

DETAILED DESCRIPTION

Figure 1:
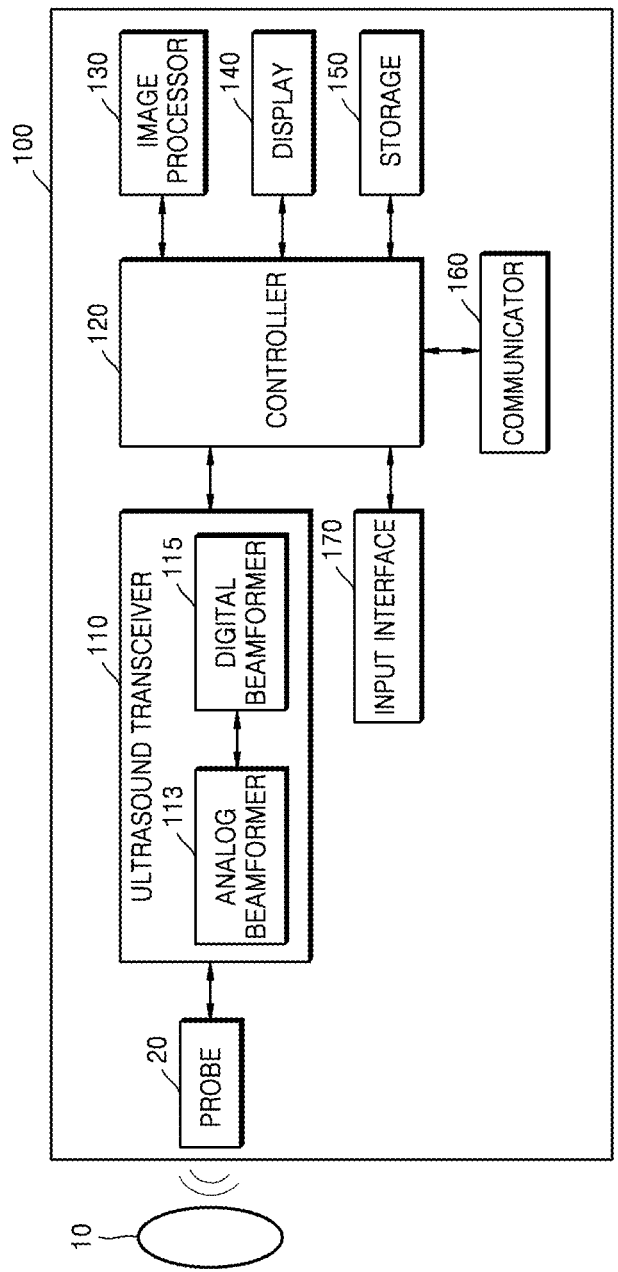
FIG. 1 is a block diagram illustrating an ultrasound diagnosis apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

In the present embodiment, the probe 20 may include a plurality of transducers. The transducers are arranged in two dimensions (2D), forming a 2D transducer array.

For example, the 2D transducer array may include a plurality of sub-arrays arranged in a first direction, each of the sub-arrays including a plurality of transducers arranged in a second direction that is different from the first direction.

The ultrasound transceiver 110 may include an analog beamformer 113 and a digital beamformer 115. Although FIG. 1 illustrates that the ultrasound transceiver 110 and the probe 20 are provided as being separate from each other, the probe 20 according to the present exemplary embodiment may include the entire ultrasound transceiver 110 or a part of the ultrasound transceiver 110.

For example, the probe 20 may include one or both of the analog beamformer 113 and the digital beamformer 115.

The controller 120 may calculate a time delay value for digital beamforming with respect to the sub-arrays included in the 2D transducer array. Also, the controller 120 may calculate a time delay value for analog beamforming for each of the transducers included in any one sub-array of the sub-arrays.

The controller 120 may control the analog beamformer 113 and the digital beamformer 115 to form a transmission signal to be applied to each of the transducers, according to the time delay values for analog beamforming and digital beamforming.

Also, the controller 120 may control the analog beamformer 113 to add signals received from the transducers for each sub-array, according to the time delay value for analog beamforming. Also, the controller 120 may control the ultrasound transceiver 110 to perform analog to digital conversion of the signals added for each sub-array. Also, the controller 120 may control the digital beamformer 115 to generate ultrasound data by adding the digitized signals according to the time delay value for digital beamforming.

The image processor 130 generates an ultrasound image by using generated ultrasound data.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
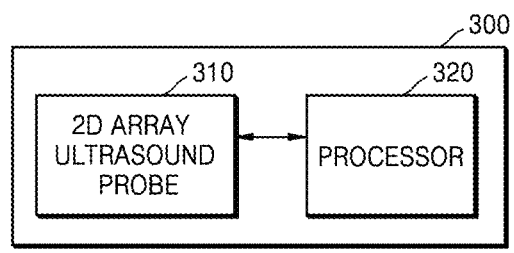
FIG. 3 is a block diagram of a structure of an ultrasound diagnosis apparatus according to an embodiment.

FIG. 3 is a block diagram of a structure of an ultrasound diagnosis apparatus 300 according to an embodiment.

Referring to FIG. 3, the ultrasound diagnosis apparatus 300 according to the present embodiment includes a two-dimensional (2D) array ultrasound probe 310 and a processor 320.

The 2D array ultrasound probe 310 shown in FIG. 3 may correspond to the probe 20 described with reference to FIG. 1, and the processor 320 may correspond to one of the image processor 130 and the controller 120 described with reference to FIG. 1 or a combination thereof. Furthermore, the processor 320 may include one or more processors (not shown). According to an embodiment, some of the components of the ultrasound diagnosis apparatus 100 of FIG. 1 may be included in the ultrasound diagnosis apparatus 300 of FIG. 3.

The 2D array ultrasound probe 310 may be implemented as a wired or wireless probe.

The 2D array ultrasound probe 310 emits focused beams onto a plurality of focusing points and detects echo signals therefrom.

According to an embodiment, the 2D array ultrasound probe 310 may induce a displacement in tissue of an object by emitting a focused beam onto the object. For example, a beamformer may adjust delays for a specific number of transducer elements to generate a focused beam that is emitted onto the object. Furthermore, after emitting the focused beams onto the object, the 2D array ultrasound probe 310 may detect echo signals from the object and acquire shear wave elasticity data necessary for generating an elastography image.

Ultrasound waves transmitted to generate shear waves that propagate into the object are referred to as a "focused beam," and a focal point onto which the focused beam is emitted is referred to as a "focusing point."

In an embodiment, when the 2D array ultrasound probe 310 emit focused beams onto a plurality of focusing points, shear waves that propagate outwards in all directions respectively from the plurality of focusing points may be generated. Furthermore, a wave front of the shear waves generated at the plurality of focusing points may travel as a waveform of a plane wave.

According to an embodiment, the 2D array ultrasound probe 310 may simultaneously emit focused beams onto a plurality of focusing points.

According to another embodiment, the 2D array ultrasound probe 310 may sequentially emit focused beams onto a plurality of focusing points.

In an embodiment, the 2D array ultrasound probe 310 may include a plurality of transducer elements arranged in a 2D matrix. Furthermore, the plurality of transducer elements in the 2D array ultrasound probe may be categorized into a plurality of element groups. According to an embodiment, in response to electrical driving signals from the processor 320, the 2D array ultrasound probe 310 may emit focused beams onto a plurality of focusing points based on element groups determined as element groups respectively corresponding to positions of the plurality of focusing points.

The processor 320 controls all operations of the ultrasound diagnosis apparatus 300 and processes data and signals. The processor 310 may include one or more processors. The processor 310 may be implemented as one or more software modules created by executing program code stored in the storage (150 of FIG. 1).

The processor 320 determines a plurality of focusing points on a cross-section of interest and acquires shear wave elasticity data with respect to the cross-section of interest from detected echo signals.

According to an embodiment, the processor 320 may determine a cross-section of interest with respect to which shear wave elasticity data is to be acquired.

In the present specification, a "cross-section of interest" may be a desired cross-section of an object including a region of interest (ROI) in a three-dimensional (3D) space with respect to which shear wave elasticity data is to be acquired. Furthermore, in the specification, an "ROI" may be a region or point of an object included in a 3D space, the region including a lesion, etc. For example, the ROI may be a region including a lesion such as a tumor located in an abdominal cavity of the object.

The processor 320 may determine a cross-section of interest based on an input received from a user or a cross-section of interest including an ROI based on a result of a specific arithmetic operation.

According to an embodiment, the processor 320 may determine a plurality of points on a cross-section of interest as being focusing points. The processor 320 may determine a plurality of points on the cross-section of interest, which lie outside an ROI, as focusing points.

In an embodiment, the processor 320 may determine a plurality of points on a straight line in a cross-section of interest as being focusing points. The processor 320 may determine a plurality of points on a straight line that is a specific distance away from an ROI as focusing points.

Furthermore, the processor 320 may determine a straight line on a cross-section of interest based on a user input or a result of a specific arithmetic operation and then a plurality of points on the determined straight line as being focusing points. The processor 320 may determine points on a straight line, which are spaced at specific intervals as being a plurality of focusing points.

According to an embodiment, the processor 320 may determine the number of a plurality of focusing points on a cross-section of interest based on a user input or a result of a specific arithmetic operation.

In an embodiment, the processor 320 may generate a driving signal for controlling the 2D array ultrasound probe 310 to simultaneously emit focused beams onto a plurality of focusing points.

According to an embodiment, the processor 320 may determine a plurality of points on a first straight line in a cross-section of interest as a first focusing group and determine a plurality of points on a second straight line in the cross-section of interest, which is distinguished from the first straight line, as a second focusing group. The processor 320 may determine the points in the first focusing group and those in the second focusing group as being a plurality of focusing points.

According to an embodiment, the processor 320 may generate a driving signal for controlling the 2D array ultrasound probe 310 to simultaneously emit focused beams onto the points in the first focusing group, lying on the first straight line, and the points in the second focusing group, lying on the second straight line.

According to another embodiment, the processor 320 may generate a driving signal for controlling the 2D array ultrasound probe 310 to emit focused beams onto the points in the first focusing group and which lie on the first straight line and emit, after a lapse of an interval of a first time, focused beams onto the points in the second focusing group and which lie on the second straight line.

When a focused beam is emitted onto the object, a displacement may be induced in the object due to propagation of shear waves, and shear wave elasticity data with respect to the object may be acquired based on the displacement induced in the object. However, when the induced displacement is not recovered, shear wave elasticity data acquired by emitting a focused beam again may not contain accurate elasticity information of the object. Thus, the processor 320 may determine a sufficient time to recover a displacement induced in the object by propagation of shear waves as being a first time.

In an embodiment, the processor 320 may determine element groups respectively corresponding to positions of a plurality of focusing points among a 2D matrix array in the 2D array ultrasound probe 310.

The 2D array ultrasound probe 310 may include a plurality of transducer elements arranged in a 2D matrix. Furthermore, the plurality of transducer elements in the 2D array ultrasound probe 310 may be categorized into a plurality of element groups. For example, the 2D array ultrasound probe 310 may include about ten thousand (10,000) transducer elements, and a total of about 10,000 transducer elements may be categorized into 10 element groups, each element group containing about one thousand (1,000) transducer elements.

The processor 320 may generate electrical driving signals to individually control element groups in the 2D array ultrasound probe 310. The processor 320 may determine element groups that are respectively to emit focused beams onto a plurality of focusing points and generate electrical driving signals for controlling the determined element groups.

According to embodiments, by simultaneously emitting focused beams onto a plurality of focusing points by using the 2D array ultrasound probe 310 including a 2D matrix array, the processor 320 may acquire 2D shear wave elasticity data with respect to a cross-section of an object in a 3D space.

According to embodiments, the processor 320 is configured to generate driving signals for individually controlling element groups in the 2D array ultrasound probe 310, thereby increasing flexibility in selecting positions of points in an object in a 3D space, which can be determined as a focusing point. Accordingly, a position and an angle of a cross-section of interest of the object in the 3D space, with respect to which 2D shear wave elasticity data is to be acquired by the processor 320, may be determined without limitation.

Furthermore, since the processor 320 may simultaneously emit focused beams onto a determined plurality of focusing points without a time delay, the position and angle of a cross-section of interest of the object in the 3D space, with respect to which 2D shear wave elasticity data is to be acquired, may not be limited.

According to an embodiment, the processor 320 may determine a plurality of points located at the same distance from an ROI or a point of interest (POI) of the object in the 3D space as being focusing points. Furthermore, the processor 320 may determine a plurality of points on a circumference surrounding as focusing points.

The processor 320 may generate driving signals for controlling the 2D array ultrasound probe 310 to simultaneously emit focused beams onto a plurality of focusing points on a circumference surrounding an ROI. When focused beams are simultaneously emitted onto the focusing points on the circumference, shear waves respectively generated at the focusing points may travel in a direction that they converge towards the ROI.

According to an embodiment, by simultaneously emitting focused beams onto a plurality of focusing points that are located at the same distance from an ROI or POI, it is possible to concentrate a relatively strong energy on the ROI or POI, as will be described in more detail below with reference to FIGS. 9A and 9B.

In an embodiment, the ultrasound diagnosis apparatus 300 may further include a user input interface (not shown) configured to receive an input of at least one of a cross-section of interest of an object in a 3D space, the number of a plurality of focusing points, and an interval between each of the plurality of focusing points. The user input interface may correspond to the input interface 170 described with reference to FIG. 1.

According to an embodiment, the ultrasound diagnosis apparatus 300 may further include a display (not shown). The display may correspond to the display 140 described with reference to FIG. 1.

In an embodiment, the display may display acquired shear wave elasticity data. The display may display shear wave elasticity data and a B-mode image of the object overlapping each other.

In another embodiment, the display may display a B-mode image in a first area on a screen and shear wave elasticity data in a second area thereon that is distinguished from the first area.

According to an embodiment, the display may display a user interface for acquiring shear wave elasticity data. The display may display the user interface in a first area on the screen. Furthermore, the display may display, in a second area that is distinguished from the first area, a graphical indicator showing status information of a cross-section of interest and focusing points thereon, which varies according to an input received via the user interface. Detailed descriptions thereof will be set forth below with reference to FIG. 8.

Figure 4A:
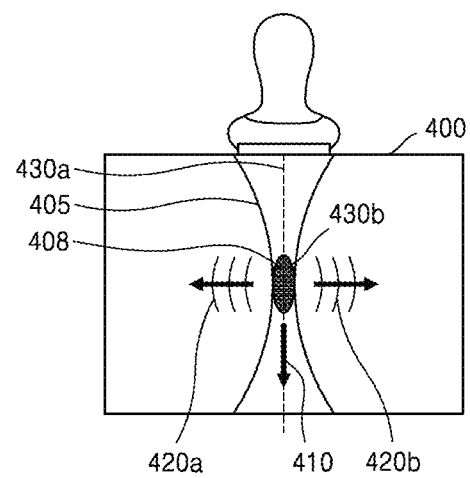
FIG. 4A illustrates a process of generating shear waves in an object according to an embodiment.

FIG. 4A illustrates a process of generating shear waves in an object according to an embodiment.

In an embodiment, the ultrasound diagnosis apparatus 300 may induce a displacement 410 of an object 400 by emitting a focused beam 405 onto a focusing point 408 of the object 400 in a 3D space. When the focused beam 405 is emitted onto the object 400, the displacement 410 of the object 400 may be induced at the focusing point 408 where the focused beam 405 is focused. Due to the displacement 410 of the object 400, shear waves 420a and 420b propagating in directions perpendicular to the displacement 400 are generated at a point where the displacement 410 occurs. The shear waves 420a and 420b generated at the focusing point 408 travel along the directions perpendicular to the displacement 410 and gradually attenuate and disappear. A mode in which shear waves in the object 400 are captured is referred to as a shear wave elasticity mode, and the shear wave elasticity mode may include a 2D shear wave elasticity measurement mode and a point shear wave elasticity measurement mode.

According to an embodiment, the ultrasound diagnosis apparatus 300 may generate shear waves in the object by emitting focused beams onto a determined plurality of focusing points.

FIG. 4B illustrates propagation of shear waves according to an embodiment.

In an embodiment, generated shear waves induce a displacement 430a at a focusing point, and as operations S450, S470, and S490 proceed sequentially, they gradually propagate along directions 440a and 440b that are perpendicular to the displacement 430a.

Figure 5:
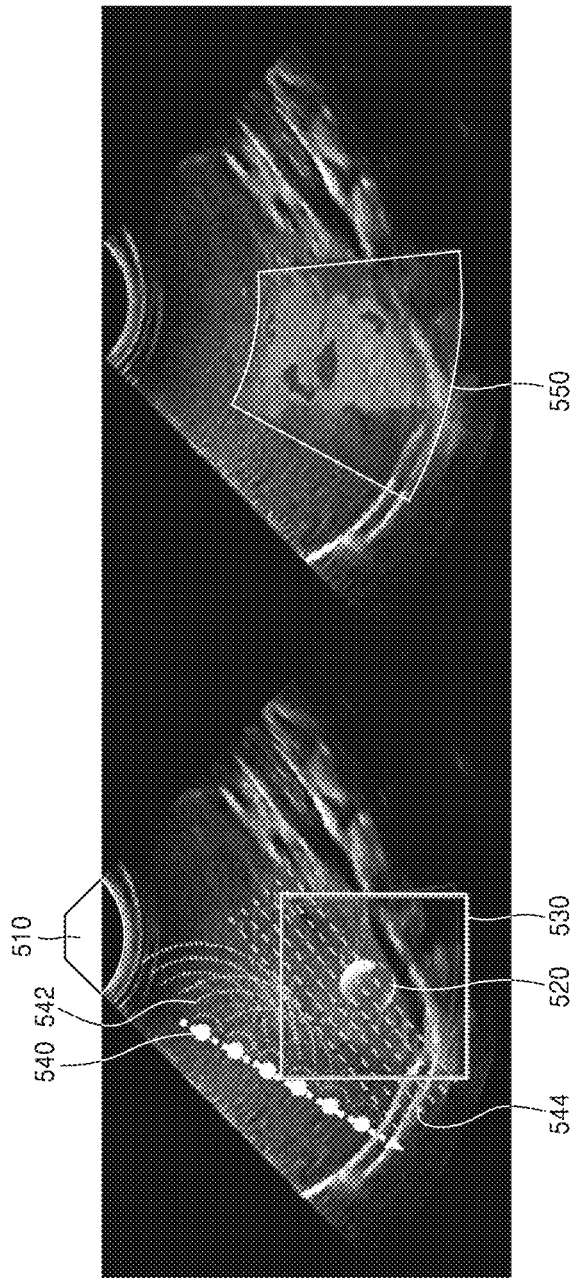
FIG. 5 is a diagram for explaining a method of acquiring shear wave elasticity data with respect to an object, according to an embodiment.

FIG. 5 is a diagram for explaining a method of acquiring shear wave elasticity data with respect to an object, according to an embodiment.

FIG. 5 illustrates a configuration in which 2D shear wave elasticity data 550 is acquired by a conventional one-dimensional (1D) ultrasound probe 510. To acquire the 2D shear wave elasticity data 550 with respect to an ROI 530 including a lesion 520 by using the 1D ultrasound probe 510, the 1D ultrasound probe 510 needs to sequentially emit focused beams onto a plurality of focusing points 540.

Referring to FIG. 5, when the 1D ultrasound probe 410 sequentially emits focused beams onto the focusing points 540 in an order that the focusing points 540 are located in a direction indicated by an arrow, shear waves 542 are respectively generated at the focusing points 540. In this case, due to time delays between the focused beams respectively emitted onto the focusing points 540, a wave front of a plane wave 544 created by the shear waves 542 generated at the focusing points 540 is tilted at a specific angle relative to a straight line on which the focusing points 540 are located.

Thus, use of the 1D ultrasound probe 510 has a problem in that a position of a cross-section of interest, with respect to which 2D shear wave elasticity data 550 is to be acquired by sequentially emitting focused beams onto the focusing points 540 and transmitting the plane wave 544 to an object 520, may be limited.

Figure 6A:
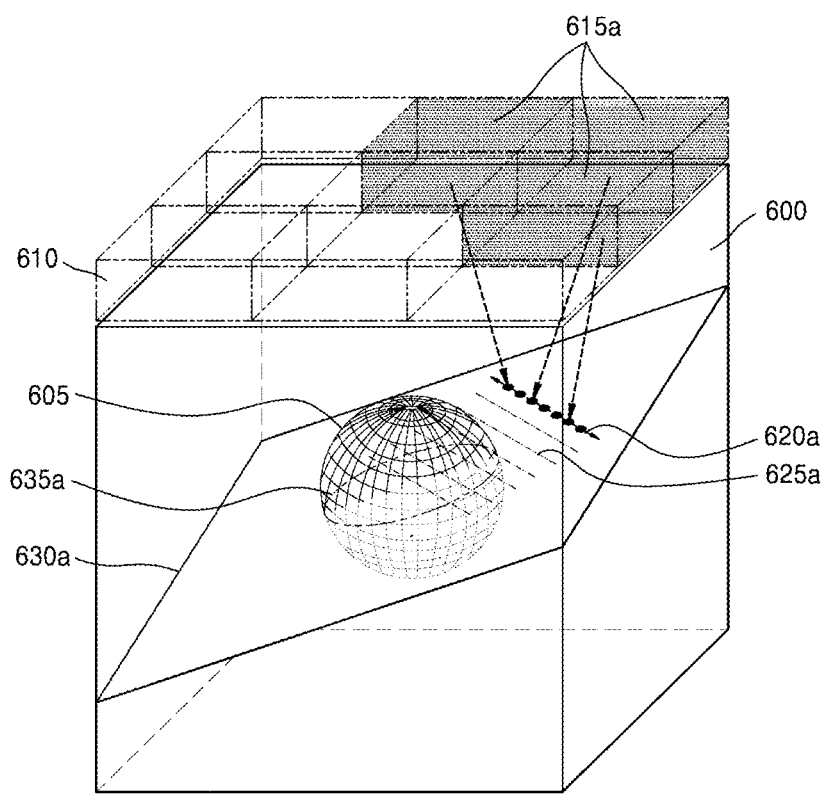
FIGS. 6A through 6C are diagrams for explaining methods of acquiring shear wave elasticity data with respect to an object by using a two-dimensional (2D) array ultrasound probe, according to an embodiment.
Figure 6B:
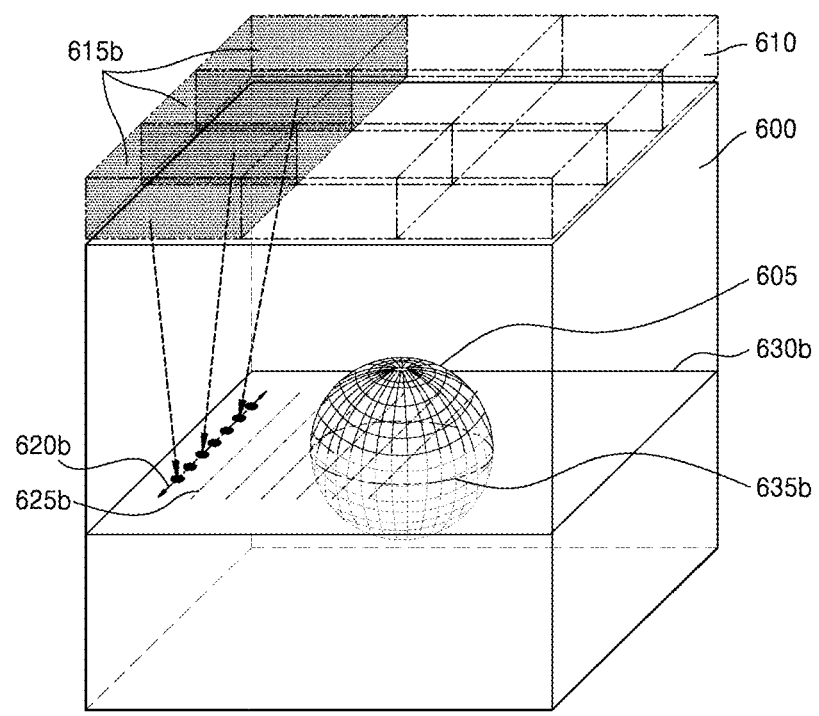
Figure 6C:
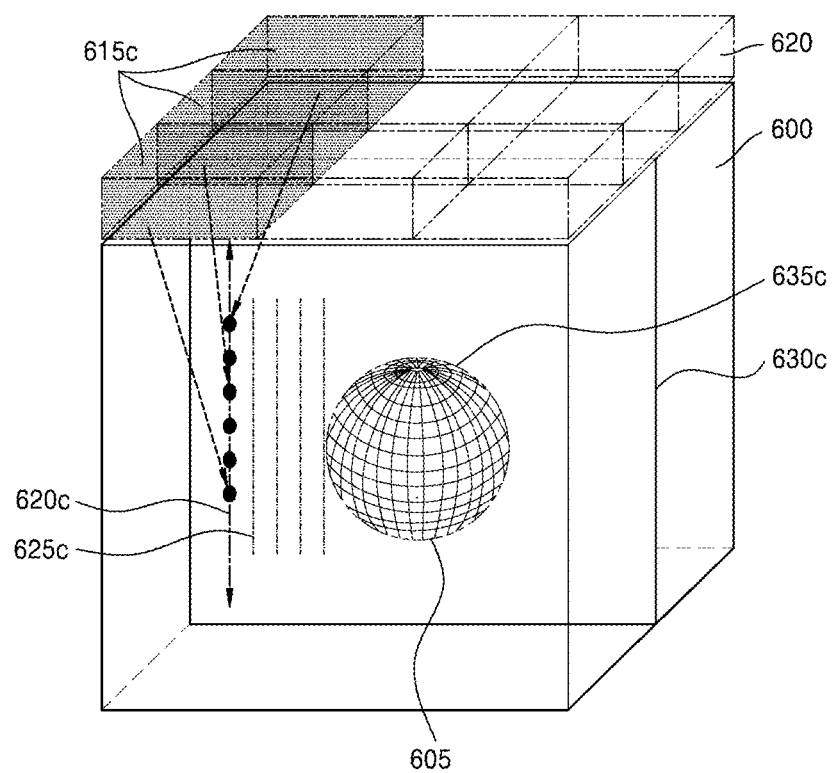

FIGS. 6A through 6C are diagrams for explaining methods of acquiring shear wave elasticity data with respect to an object by using the 2D array ultrasound probe 310, according to an embodiment.

FIG. 6A illustrates a method whereby the ultrasound diagnosis apparatus 300 acquires shear wave elasticity data with respect to a cross-section of interest 630a of an object in a 3D space 600 by using the 2D array ultrasound probe 310 including a 2D matrix transducer array 610.

In an embodiment, the ultrasound diagnosis apparatus 300 may determine a plurality of focusing points 620a in order to acquire 2D shear wave elasticity data with respect to the cross-section of interest 630a of the objet in the 3D space 600.

According to an embodiment, the ultrasound diagnosis apparatus 300 may determine a plurality of points on the cross-section of interest 630a, which lie outside an ROI 605, as a plurality of focusing points 620a. For example, the ultrasound diagnosis apparatus 300 may determine a plurality points on the cross-section of interest 630a, which are not included in a cross-section 635a of the ROI 605, as the focusing points 620a.

According to an embodiment, the determined focusing points 620a may be points on a straight line in the cross-section of interest 630a.

The ultrasound diagnosis apparatus 300 may simultaneously emit focused beams onto the focusing points 620a. To achieve this, the ultrasound diagnosis apparatus 300 may determine element groups 615a respectively corresponding to positions of the focusing points 620a among the 2D matrix transducer array 610 of the 2D array ultrasound probe 310. The ultrasound diagnosis apparatus 300 may generate electrical driving signals for controlling the determined element groups 615*a* to simultaneously emit focused beams onto the focusing points 620*a*.

When the focused beams are simultaneously emitted onto the focusing points 620*a*, a plane wave 625*a* propagating parallel to a straight line where the focusing points 620*a* are located may be created due to shear waves generated at the focusing points 620*a*. The ultrasound diagnosis apparatus 300 may detect echo signals with respect to the cross-section of interest 630*a* of the object in the 3D space 600 based on the plane wave 625*a*. Furthermore, the ultrasound diagnosis apparatus 300 may acquire 2D shear wave elasticity data with respect to the cross-section of interest 630*a* based on the detected echo signals. The ultrasound diagnosis apparatus 300 may acquire 2D shear wave elasticity data with respect to the ROI 605 based on the 2D shear wave elasticity data with respect to the cross-section of interest 630*a*.

FIG. 6B illustrates a method whereby the ultrasound diagnosis apparatus 300 acquires shear wave elasticity data with respect to a cross-section of interest 630*b* of an object in a 3D space 600 by using the 2D array ultrasound probe 310 including a 2D matrix transducer array 610. The cross-section of interest 630*b* may be a cross-section that is parallel to the 2D matrix transducer array 610 and includes an ROI 605.

Descriptions of a method, performed by the ultrasound diagnosis apparatus 300, of determining a plurality of focusing points 620*b* in order to acquire 2D shear wave elasticity data with respect to the cross-section of interest 630*b* of the object in the 3D space 600 according to an embodiment and a method, performed by the ultrasound diagnosis apparatus 300, of acquiring the 2D shear wave elasticity data by simultaneously emitting focused beams onto the focusing points 620*b* according to an embodiment are already provided above with respect to FIG. 6A, and thus, are not repeated.

FIG. 6C illustrates a method whereby the ultrasound diagnosis apparatus 300 acquires shear wave elasticity data with respect to a cross-section of interest 630*c* of an object in a 3D space 600 by using the 2D array ultrasound probe 310 including a 2D matrix transducer array 610. The cross-section of interest 630*c* may be a cross-section that is perpendicular to the 2D matrix transducer array 620 and includes an ROI 605.

Descriptions of a method, performed by the ultrasound diagnosis apparatus 300, of determining a plurality of focusing points 620*c* in order to acquire 2D shear wave elasticity data with respect to the cross-section of interest 630*c* of the object in the 3D space 600 and a method, performed by the ultrasound diagnosis apparatus 300, of acquiring the 2D shear wave elasticity data by simultaneously emitting focused beams onto the focusing points 620*c* are already provided above with respect to FIG. 6A, and thus, are not repeated.

According to embodiments, by simultaneously emitting focused beams onto a plurality of focusing points by using the 2D array ultrasound probe 310 including a 2D matrix transducer array, the ultrasound diagnosis apparatus 300 may acquire 2D shear wave elasticity data with respect to a cross-section of an object in a 3D space.

According to embodiments, the ultrasound diagnosis apparatus 300 is configured to generate driving signals for individually controlling element groups in the 2D array ultrasound probe 310, thereby increasing flexibility in selecting positions of points of an object in a 3D space, which can be determined as a focusing point. Accordingly, a position and an angle of a cross-section of interest of the object in the 3D space, with respect to which 2D shear wave elasticity data is to be acquired by the ultrasound diagnosis apparatus 300, may not be limited.

Furthermore, since the ultrasound diagnosis apparatus 300 may simultaneously emit focused beams onto a determined plurality of focusing points without a time delay, the position and angle of a cross-section of interest of the object in the 3D space, with respect to which 2D shear wave elasticity data is to be acquired, may not be limited.

Figure 7:
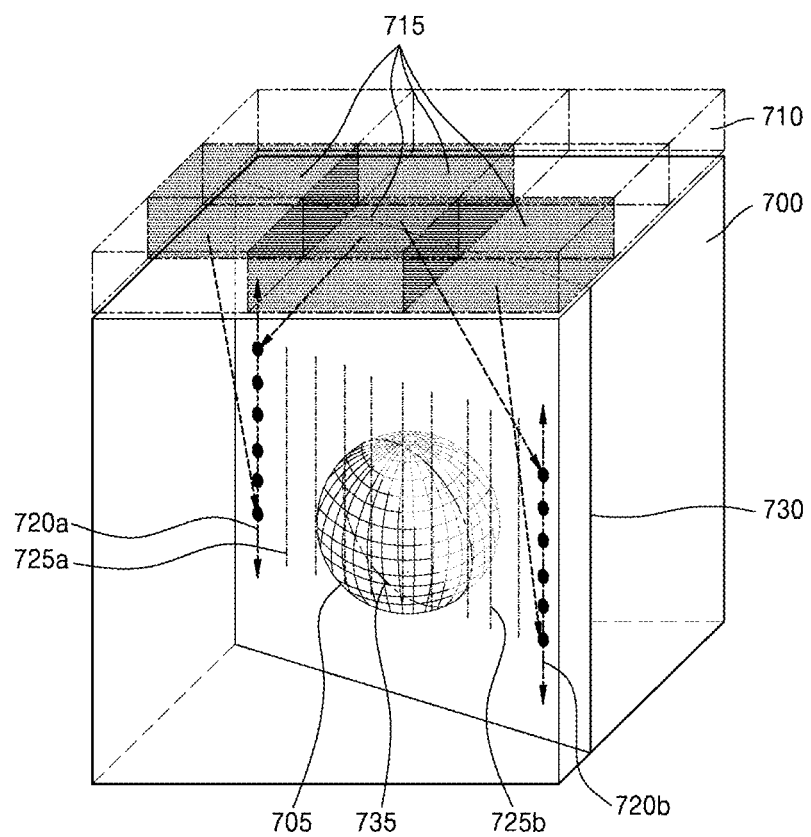
FIG. 7 is a diagram for explaining a method of acquiring shear wave elasticity data with respect to an object by using a 2D array ultrasound probe, according to another embodiment.

FIG. 7 is a diagram for explaining a method of acquiring shear wave elasticity data with respect to an object by using the 2D array ultrasound probe 310, according to another embodiment.

FIG. 7 illustrates a method whereby the ultrasound diagnosis apparatus 300 acquires shear wave elasticity data with respect to a cross-section of interest 730 of an object in a 3D space 700 by using the 2D array ultrasound probe 310 including a 2D matrix transducer array 710.

According to an embodiment, the ultrasound diagnosis apparatus 300 may determine a plurality of points on a first straight line 720*a* in the cross-section of interest 730 as a first focusing group and determine a plurality of points on a second straight line 720*b* in the cross-section of interest 730, which is distinguished from the first straight line 720*a*, as a second focusing group. The first and second straight lines 720*a* and 720*b* may be straight lines in the cross-section of interest 730, which do not pass through an ROI 705. Furthermore, in an embodiment, the first and second straight lines 720*a* and 720*b* may be parallel straight lines with a cross-section 735 of the ROI 705 interposed therebetween.

According to an embodiment, the ultrasound diagnosis apparatus 300 may simultaneously emit focused beams onto the plurality of points in the first focusing group, lying on the first straight line 720*a*, and the plurality of points in the second focusing group, lying on the second straight line 720*b*.

In order to simultaneously emit focused beams onto the points in the first and second focusing groups, respectively lying on the first and second straight lines 720*a* and 720*b*, the ultrasound diagnosis apparatus 300 may determine element groups 715 respectively corresponding to positions of the plurality of focusing points on the first and second straight lines 720*a* and 720*b*, among the 2D matrix transducer array 710 of the 2D array ultrasound probe 310. The ultrasound diagnosis apparatus 300 may generate electrical driving signals for controlling the determined element groups 715 to simultaneously emit focused beams onto the plurality of focusing points.

When focused beams are simultaneously emitted onto the points in the first and second focusing groups, lying on the first and second straight lines 720*a* and 720*b*, plane waves 725*a* and 725*b* respectively propagating parallel to the first and second straight lines 720*a* and 720*b* may be created. The ultrasound diagnosis apparatus 300 may detect echo signals with respect to the cross-section of interest 730 based on the plane waves 725*a* and 725*b*. The ultrasound diagnosis apparatus 300 may acquire, based on the detected echo signals, 2D shear wave elasticity data with respect to the cross-section of interest 730, which is created by overlapping shear wave elasticity data from different points of view with each other.

According to another embodiment, the ultrasound diagnosis apparatus 300 may emit focused beams onto the points in the first focusing group and which lie on the first straight line 720*a* and emit, after a lapse of an interval of a first time, focused beams onto the points in the second focusing group and which lie on the second straight line 720b. The ultrasound diagnosis apparatus 300 may determine sufficient time to recover a displacement induced in the object due to propagation of shear waves as being the first time.

According to embodiments, the ultrasound diagnosis apparatus 300 may acquire 2D shear wave elasticity data with respect to the cross-section of interest 730, which is created by overlapping shear wave elasticity data from different points of view each other. Thus, relatively high quality 2D shear wave elasticity data may be obtained. Furthermore, such acquisition of 2D shear wave elasticity data may prevent a lesion from going undetected due to a shadow effect.

Figure 8:
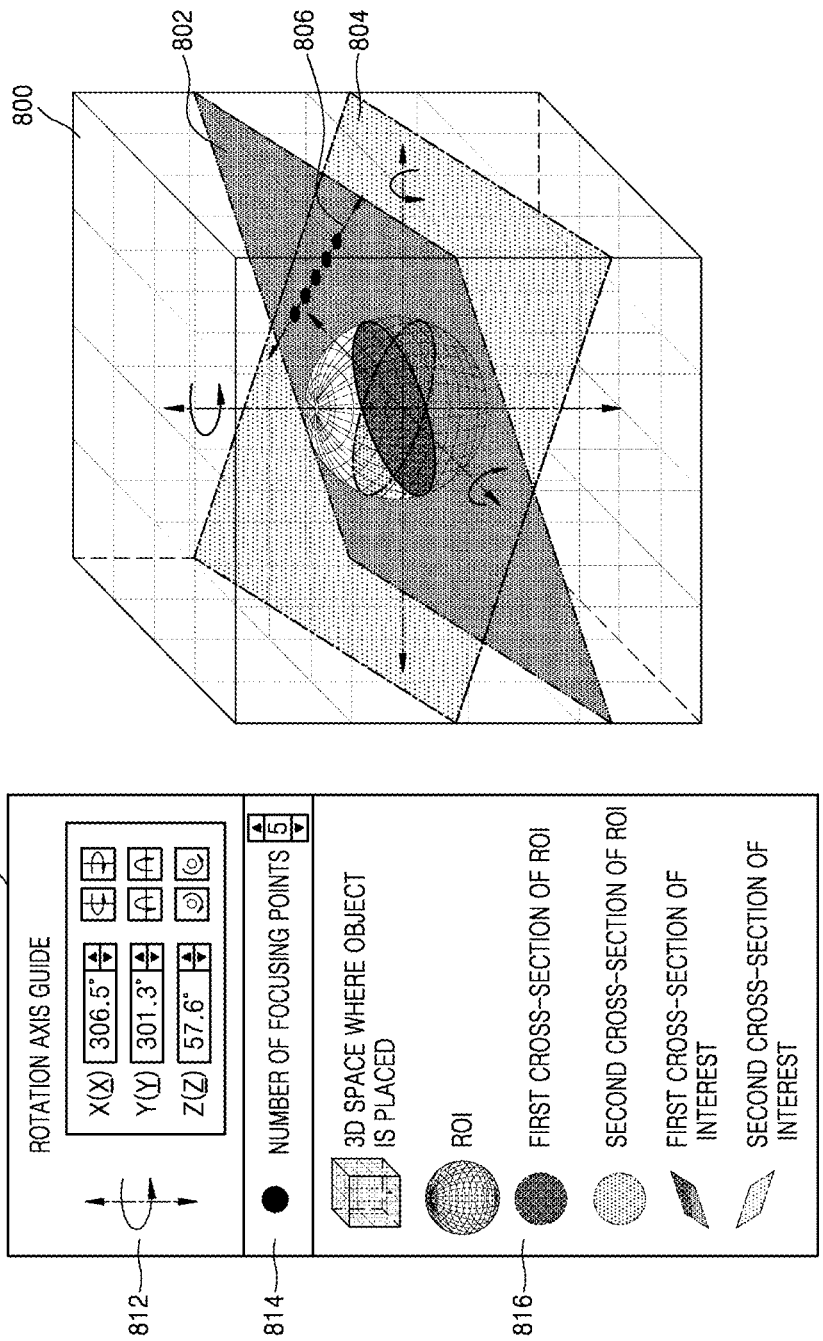
FIG. 8 illustrates a user interface for acquiring shear wave elasticity data according to an embodiment.

FIG. 8 illustrates a user interface 810 for acquiring shear wave elasticity data according to an embodiment.

Referring to FIG. 8, the ultrasound diagnosis apparatus 300 may display, in a first area on a display screen, the user interface 810 for receiving an input with respect to a cross-section of interest of an object in a 3D space and focusing points.

The ultrasound diagnosis apparatus 300 may display, in a second area on the display screen that is distinguished from the first area, a graphical indicator 800 showing status information of a cross-section of interest and focusing points, which varies according to an input received via the user interface 810.

According to another embodiment, the ultrasound diagnosis apparatus 300 may display the graphical indicator 800 in a second area of which the entire or some region overlaps a first area on the display screen.

According to an embodiment, the graphical indicator 800 may be displayed in such a manner as to overlap an image of the object.

According to an embodiment, the user interface 810 may include a rotation axis guide 812 for changing a rotation angle of a cross-section of interest of the object in the 3D space. For example, the user may input a rotation angle with respect to at least one of X- Y- and Z-axes, which is included in the rotation axis guide 812, to change an angle and a direction of a cross-section of interest of the object in the 3D space.

Furthermore, the ultrasound diagnosis apparatus 300 may receive a user input for changing a rotation angle of each of a plurality of cross-sections of interest, i.e., first and second cross-sections of interest 802 and 804, via the user interface 810. For example, if the user desires to change a rotation angle of the first cross-section of interest 802, the user may select and activate the first cross-section of interest 802 of the object in the 3D space, viewed on the graphical indicator 800, and input a rotation angle thereof with respect to at least one of the X- Y- and Z-axes, included in the rotation axis guide 812, to change an angle and a direction of the first cross-section of interest 802. Furthermore, if the user desires to change a rotation angle of the second cross-section of interest 804, the user may select and activate the second cross-section of interest 804 of the object in the 3D space, viewed on the graphical indicator 800, and input a rotation angle thereof with respect to at least one of the X- Y- and Z-axes, included in the rotation axis guide 812, to change an angle and a direction of the second cross-section of interest 804.

In an embodiment, the user interface 810 may include an input box 814 for entering the number of a plurality of focusing points on a cross-section of interest.

In an embodiment, the graphical indicator 800 may show information about a plurality of focusing points on a cross-section of interest, which is received via the input box 814 in the user interface 810. For example, if '5' is entered into the input box 814 by the user, the ultrasound diagnosis apparatus 300 may display five (5) points 806 on the first or second cross-section of interest 802 or 804 shown on the graphical indicator 800. Furthermore, the ultrasound diagnosis apparatus 300 may change positions of the five points 806 on the first or second cross-section of interest 802 or 804 according to a user input for selecting and dragging the five points 806 shown on the graphical indicator 800.

According to an embodiment, the user interface 810 may include a description box 816 for graphical entities shown on the graphical indicator 800. For example, the description box 816 may include descriptions of graphical entities respectively corresponding to a 3D space where an object is placed, an ROI, a first cross-section of the ROI, a second cross-section of the ROI, a first cross-section of interest, and a second cross-section of interest.

Figure 9A:
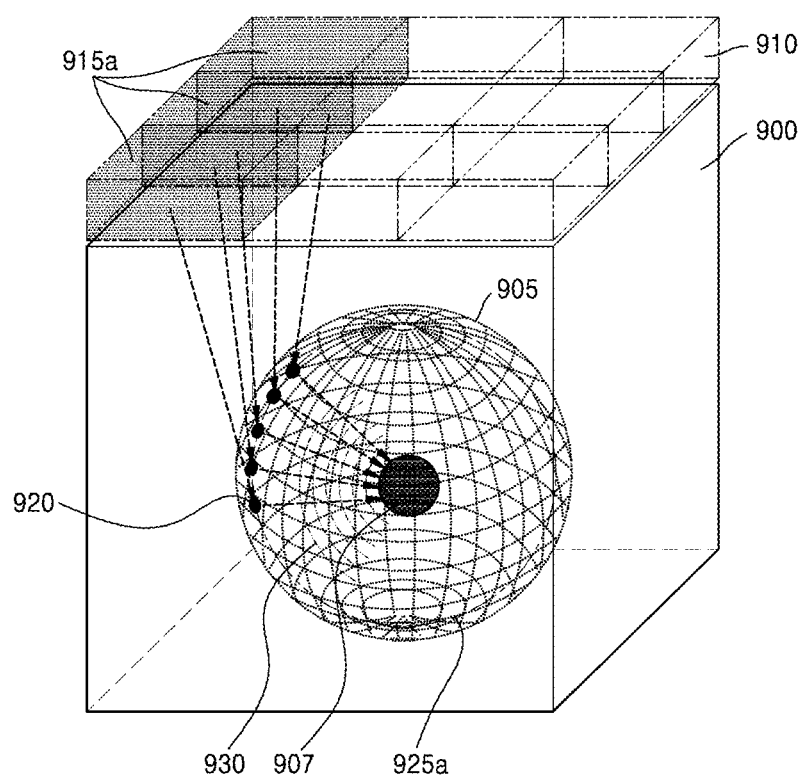
FIGS. 9A and 9B are diagrams for explaining methods of acquiring shear wave elasticity data with respect to an object by using a 2D array ultrasound probe, according to another embodiment.
Figure 9B:
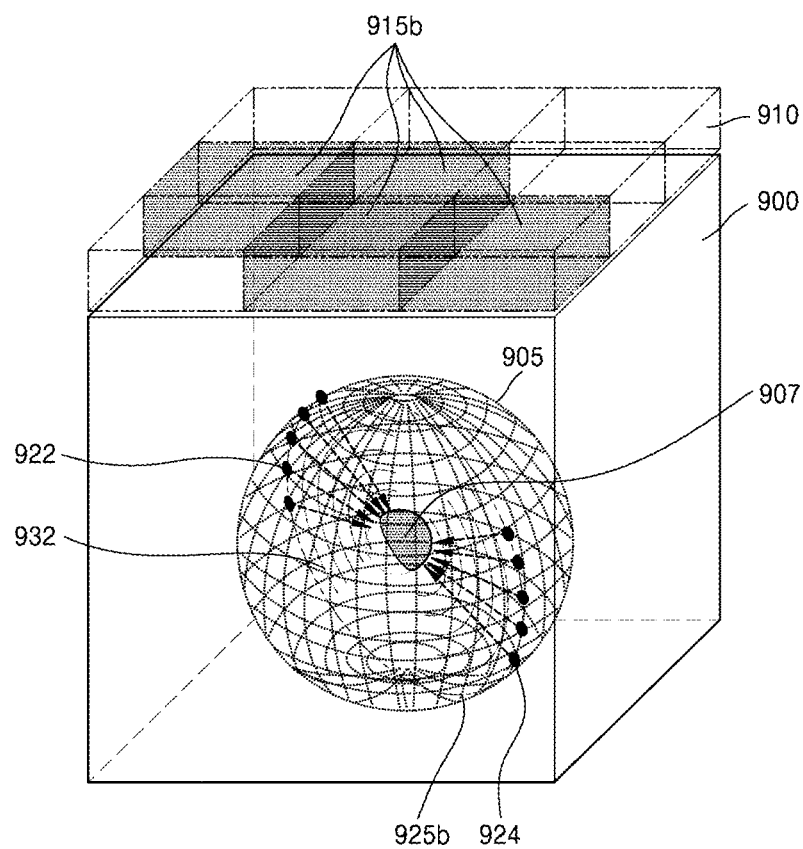

FIGS. 9A and 9B are diagrams for explaining a method of acquiring shear wave elasticity data with respect to an object by using the 2D array ultrasound probe 310, according to another embodiment.

FIG. 9A illustrates a method whereby the ultrasound diagnosis apparatus 300 converges shear waves generated at a plurality of focusing points 920 to an ROI 907 of an object in a 3D space 900 by using the 2D array ultrasound probe 310 including a 2D matrix transducer array 910.

According to an embodiment, the ultrasound diagnosis apparatus 300 may determine a plurality of points that are located at the same distance from the ROI (or POI) 907 as being focusing points. The plurality of points that are located at the same distance from the ROI 907 may be points lying on a sphere surface surrounding the ROI 907.

According to another embodiment, the plurality of points that are located at the same distance from the ROI 907 may be points lying on a circumference 925a surrounding the ROI 907.

Referring to FIG. 9A, the ultrasound diagnosis apparatus 300 may determine a plurality of points lying on the circumference 925a surrounding the ROI 907 as being the plurality of focusing points 920. The diagnosis apparatus 300 may simultaneously emit focused beams onto the focusing points 920. To achieve this, the ultrasound diagnosis apparatus 300 may determine element groups 915a respectively corresponding to positions of the focusing points 920 among the 2D matrix transducer array 910 of the 2D array ultrasound probe 310. The ultrasound diagnosis apparatus 300 may generate electrical driving signals for controlling the determined element groups 915a to simultaneously emit focused beams onto the focusing points 920.

When focused beams are simultaneously emitted onto the focusing points 920 on a circumference, shear waves 930 respectively generated at the focusing points 920 may travel in a direction that they converge towards the ROI 907.

The ultrasound diagnosis apparatus 300 may transmit a relatively large amount of energy to the ROI 907 by simultaneously emitting focused beams onto the focusing points 920 that are located at the same distance from the ROI 907.

The ultrasound diagnosis apparatus 300 may acquire shear wave elasticity data with respect to a cross-section including the ROI 907 by simultaneously emitting focused beams onto the focusing points 920 that are located at the same distance from the ROI 907 and detecting echo signals.

FIG. 9B illustrates a method whereby the ultrasound diagnosis apparatus 300 converges shear waves generated at a plurality of focusing points to an ROI 907 of an object in a 3D space 900 by using the 2D array ultrasound probe 310 including a 2D matrix transducer array 910.

In an embodiment, the ultrasound diagnosis apparatus 300 may determine a plurality of points in a first focusing group 922 and a plurality of points in a second focusing group 924, which lie on a circumference 925b and are located at symmetrical positions with respect to the ROI 907, as being a plurality of focusing points.

According to an embodiment, the ultrasound diagnosis apparatus 300 may simultaneously emit focused beams onto the plurality of points in the first focusing group 922 and those in the second focusing group 924.

In order to simultaneously emit focused beams onto the points in the first and second focusing groups 922 and 924, the ultrasound diagnosis apparatus 300 may determine element groups 915b respectively corresponding to positions of the plurality of focusing points among the 2D matrix transducer array 910 of the 2D array ultrasound probe 310. The ultrasound diagnosis apparatus 300 may generate electrical driving signals for controlling the determined element groups 915b to simultaneously emit focused beams onto the points in the first and second focusing groups 922 and 924.

According to another embodiment, the ultrasound diagnosis apparatus 300 may emit focused beams onto the points in the first focusing group 922 and emit, after a lapse of an interval of a first time, focused beams onto the points in the second focusing group 924. The ultrasound diagnosis apparatus 300 may determine sufficient time to recover a displacement induced in the object due to propagation of shear waves as being the first time.

Figure 10:
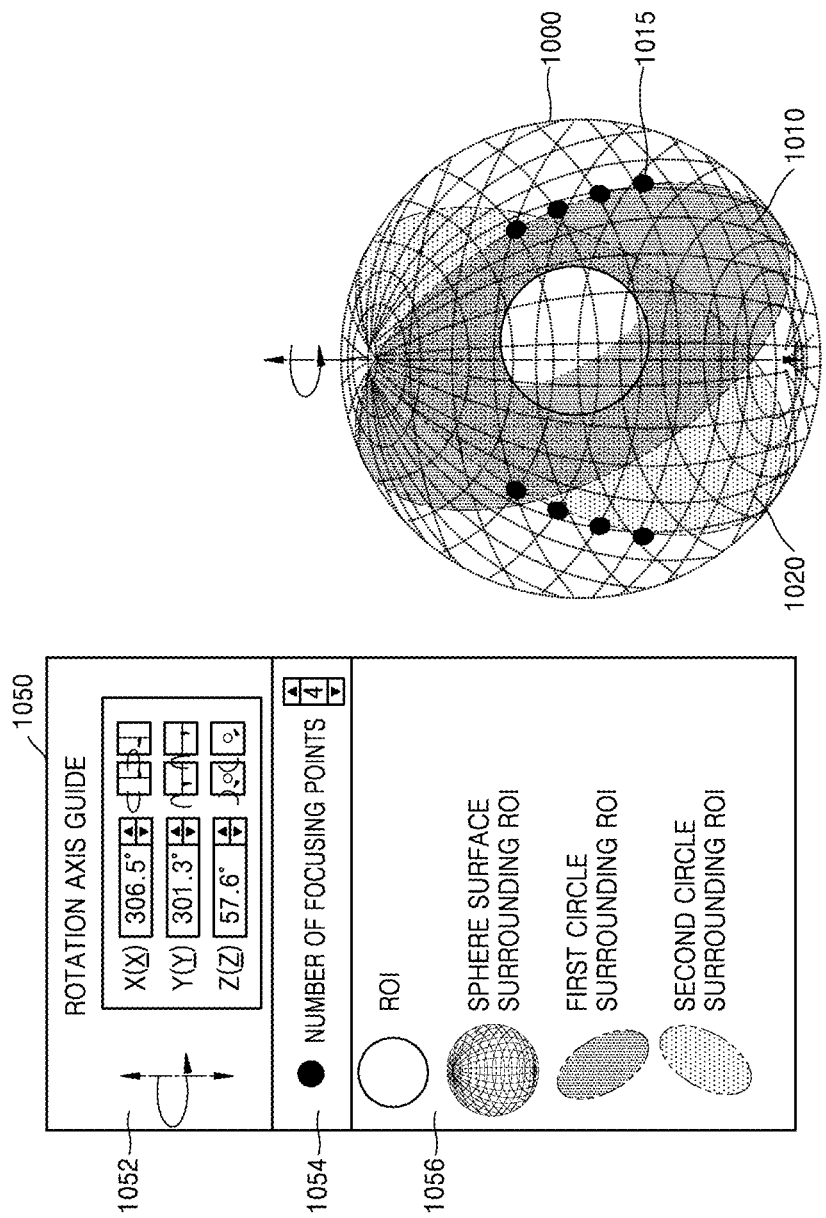
FIG. 10 illustrates a user interface for acquiring shear wave elasticity data, according to an embodiment.

FIG. 10 illustrates a user interface 1050 for acquiring shear wave elasticity data, according to an embodiment.

Referring to FIG. 10, the ultrasound diagnosis apparatus 300 may display, in a first area on a display screen, the user interface 1050 for receiving an input with respect to a circle surrounding an ROI and focusing points.

The ultrasound diagnosis apparatus 300 may display, in a second area on the display screen that is distinguished from the first area, a graphical indicator 1000 showing status information of a circle surrounding the ROI and focusing points thereon, which varies according to an input received via the user interface 1050.

According to another embodiment, the ultrasound diagnosis apparatus 300 may display the graphical indicator 1000 in a second area of which the entire or some region overlaps a first area on the display screen.

In an embodiment, the graphical indicator 1000 may be displayed in such a manner as to overlap a 3D image of the object.

According to an embodiment, the user interface 1050 may include a rotation axis guide 1052 for changing a rotation angle of a circle surrounding an ROI. For example, the user may input a rotation angle with respect to at least one of X- Y- and Z-axes, which is included in the rotation axis guide 1052, to change an angle and a direction of the circle surrounding the ROI.

Furthermore, the ultrasound diagnosis apparatus 300 may receive a user input for changing a rotation angle of each of a plurality of circles surrounding an ROI, i.e., first and second circles 1010 and 1020, via the user interface 1050. For example, if the user desires to change a rotation angle of the first circle 1010, the user may select and activate the first circle 1010 surrounding the ROI, shown on the graphical indicator 1000, and input a rotation angle thereof with respect to at least one of the X- Y- and Z-axes, included in the rotation axis guide 1052, to change an angle and a direction of the first circle 1010. Furthermore, if the user desires to change a rotation angle of the second circle 1020, the user may select and activate the second circle 1020 surrounding the ROI, shown on the graphical indicator 1000, and input a rotation angle thereof with respect to at least one of the X- Y- and Z-axes, included in the rotation axis guide 1052, to change an angle and a direction of the second circle 1020.

In an embodiment, the user interface 1050 may include an input box 1054 for entering the number of a plurality of focusing points 1015 on a circumference of a circle surrounding the ROI.

In an embodiment, the graphical indicator 1000 may show information about the plurality of focusing points 1015 on a circumference of a circle surrounding the ROI, which is received via the input box 1054 in the user interface 1050. Furthermore, the ultrasound diagnosis apparatus 300 may change positions of the focusing points 1015 on a circumference of a circle surrounding the ROI according to a user input for selecting and dragging the focusing points 1015 shown on the graphical indicator 1000.

According to an embodiment, the user interface 1050 may include a description box 1056 for graphical entities shown on the graphical indicator 800. For example, the description box 1056 may include descriptions of graphical entities respectively corresponding to an ROI, a sphere surface surrounding the ROI, a first circle surrounding the ROI, and a second circle surrounding the ROI.

Figure 11:
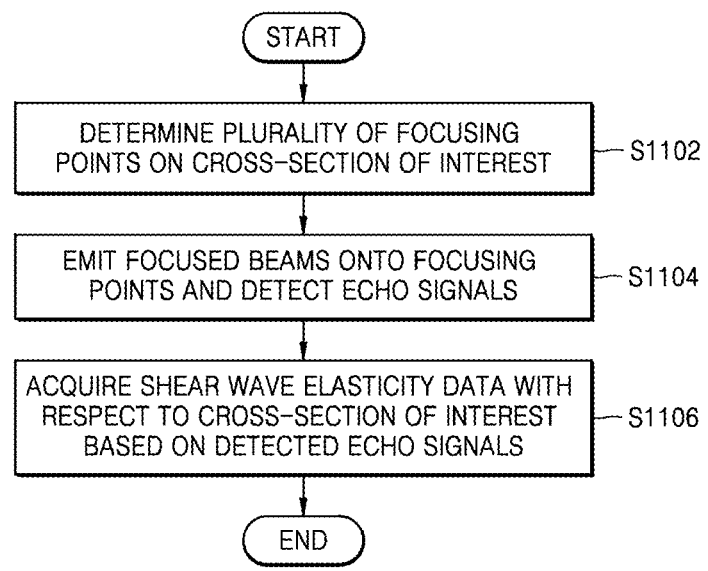
FIG. 11 is a flowchart of a method of controlling an ultrasound diagnosis apparatus, according to an embodiment.

FIG. 11 is a flowchart of a method of controlling an ultrasound diagnosis apparatus, according to an embodiment.

The method of controlling an ultrasound diagnosis apparatus according to the present embodiment may be performed by the ultrasound diagnosis apparatus 300 described above with reference to FIG. 3, and operations of the method may be substantially the same as those performed by the ultrasound diagnosis apparatus 300. Thus, descriptions that are already provided above with respect to FIG. 3 will be omitted below.

The ultrasound diagnosis apparatus 300 determines a plurality of focusing points on a cross-section of interest of an object in a 3D space (S1102).

The ultrasound diagnosis apparatus 300 emits focused beams onto the determined plurality of focusing points and detects echo signals (S1104).

The ultrasound diagnosis apparatus 300 acquires shear wave elasticity data with respect to the cross-section of interest based on the detected echo signals (S1106).

The above-described embodiments of the present inventive concept may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

What is claimed is:

1. An ultrasound diagnosis apparatus comprising:
a two-dimensional (2D) array ultrasound probe configured to transmit a plurality of focused beams generating shear waves onto a plurality of focal points corresponding to each of the plurality of focused beams and receive echo signals;
an input interface configured to receive an input to set a cross-section of interest of an object in a 3D space, a number of the plurality of focal points, and an interval between each of the plurality of focal points;

a processor configured to determine element groups of among a 2D matrix array respectively corresponding to positions of the plurality of focal points based on the input, determine the plurality of focal points on the cross-section of interest and acquire shear wave elasticity data with respect to the cross-section of interest based on the received echo signals, a display configured to display the acquired shear wave elasticity data; and wherein the processor is further configured to determine an angle of the cross-section of interest based on the input, and control the display to display the acquired shear wave elasticity data with respect to the determined angle, and the plurality of focal points are focal points onto which the plurality of focused beams are emitted, wherein the processor is further configured to determine status information of the cross-section of interest and the plurality of focal points, control the display to display the status information as a graphical indicator including an image of focal points determined by user input and an image of a first cross-section of a region of interest obtained by a focused beam of a shear wave.

2. The ultrasound diagnosis apparatus of claim 1, wherein the 2D array ultrasound probe is further configured to simultaneously transmit the plurality of focused beams to the plurality of focal points.

3. The ultrasound diagnosis apparatus of claim 1, wherein the plurality of focal points lie on a straight line in the cross-section of interest.

4. The ultrasound diagnosis apparatus of claim 1, wherein the processor is further configured to determine a plurality of focal points lying on a first straight line in the cross-section of interest as a first focusing group and determine a plurality of focal points on a second straight line in the cross-section of interest, which is distinguished from the first straight line, as a second focusing group.

5. The ultrasound diagnosis apparatus of claim 4, wherein the 2D array ultrasound probe is further configured to simultaneously transmit the plurality of focused beams to the plurality of focal points in the first focusing group and the plurality of focal points in the second focusing group.

6. The ultrasound diagnosis apparatus of claim 4, wherein the 2D array ultrasound probe is further configured to transmit the plurality of focused beams to the plurality of focal points in the first focusing group and to transmit, after a lapse of a first time interval, the plurality of focused beams to the plurality of focal points in the second focusing group.

7. The ultrasound diagnosis apparatus of claim 1,
wherein the input interface comprises an input box to receive an input of the number of the plurality of focal points, and
the processor is further configured to control the display to display the received number of the plurality of focal points on the cross-section of interest.

8. A method of controlling an ultrasound diagnosis apparatus, the method comprising:

receiving an input to set a cross-section of interest of an object in a 3D space, a number of a plurality of focal points, and an interval between each of the plurality of focal points;

determining element groups of among a 2D matrix array respectively corresponding to positions of the plurality of focal points based on the input;

determining an angle of the cross-section of interest and a plurality of focal points on the cross-section of interest based on the input;

emitting focused beams generating shear waves onto the determined plurality of focal points;

detecting echo signals;

acquiring shear wave elasticity data with respect to the cross-section of interest based on the detected echo signals;

determining status information of the cross-section of interest and the plurality of focal points;

displaying the acquired shear wave elasticity data; and displaying the status information as a graphical indicator including an image of focusing focal points determined by user input and an image of a first cross-section of the a region of interest obtained by a focused beam of a shear wave, wherein the plurality of focal points are focal points onto which the focused beams are emitted.

9. The method of claim 8, wherein the transmitting of the focused beams to the plurality of focal points comprises simultaneously transmitting the focused beams to the plurality of focal points.

10. The method of claim 8, wherein the plurality of focal points lie on a straight line in the cross-section of interest.

11. The method of claim 8, wherein the determining of the plurality of focal points comprises:
determining a plurality of focal points lying on a first straight line in the cross-section of interest as a first focusing group; and
determining a plurality of focal points on a second straight line in the cross-section of interest, which is distinguished from the first straight line, as a second focusing group.

12. The method of claim 11, wherein the transmitting of the focused beams to the plurality of focal points comprises simultaneously transmitting the focused beams to the plurality of focal points in the first focusing group and the plurality of focal points in the second focusing group.

13. The method of claim 11, wherein the transmitting of the focused beams to the plurality of focal points comprises transmitting the focused beams to the plurality of focal points in the first focusing group and transmitting, after a lapse of a first time interval, the focused beams to the plurality of focal points in the second focusing group.

14. The method of claim 8, further comprising:
receiving an input of the number of the plurality of focal points through an input box, and
displaying the received number of the plurality of focal points on the cross-section of interest.

15. A non-transitory computer-readable recording medium having recorded thereon a program for executing the method of claim 8 on a computer.

* * * * *